(12) United States Patent
King et al.

(10) Patent No.: US 11,865,310 B2
(45) Date of Patent: Jan. 9, 2024

(54) HANDHELD DRUG DELIVERY DEVICE

(71) Applicant: UNL Holdings LLC, New York, NY (US)

(72) Inventors: Andrew N. King, Malvern, PA (US); Ian B. Hanson, Wayne, PA (US); Paul F. Bente, IV, Wayne, PA (US)

(73) Assignee: UNL HOLDINGS LLC

( * ) Notice: Subject to any disclaimer, the term of this patent is extended or adjusted under 35 U.S.C. 154(b) by 212 days.

(21) Appl. No.: 16/872,230

(22) Filed: May 11, 2020

(65) Prior Publication Data

US 2021/0146057 A1   May 20, 2021

Related U.S. Application Data

(63) Continuation of application No. PCT/IB2017/001371, filed on Nov. 9, 2017.

(51) Int. Cl.
*A61M 5/20* (2006.01)
*A61M 5/315* (2006.01)
*A61M 5/24* (2006.01)

(52) U.S. Cl.
CPC ... *A61M 5/31535* (2013.01); *A61M 2005/206* (2013.01); *A61M 2005/247* (2013.01); *A61M 2205/13* (2013.01); *A61M 2205/50* (2013.01); *A61M 2205/581* (2013.01); *A61M 2205/582* (2013.01); *A61M 2205/583* (2013.01); *A61M 2205/586* (2013.01); *A61M 2205/587* (2013.01)

(58) Field of Classification Search
CPC ...... A61M 2005/206; A61M 2005/247; A61M 2005/2073
See application file for complete search history.

(56) References Cited

U.S. PATENT DOCUMENTS

| | | | | |
|---|---|---|---|---|
| 5,067,947 | A | * 11/1991 | Volk | A61M 5/3213 604/110 |
| 2006/0173408 | A1 | * 8/2006 | Wyrick | A61M 5/2033 604/110 |
| 2019/0366000 | A1 | * 12/2019 | Cowe | A61M 5/2422 |

* cited by examiner

*Primary Examiner* — Emily L Schmidt
(74) *Attorney, Agent, or Firm* — MARSHALL, GERSTEIN & BORUN LLP

(57) ABSTRACT

Handheld drug delivery devices for injection of a medicament into a target location are disclosed herein. The drug delivery devices of the present disclosure include drive mechanisms, needle insertion mechanisms, and fluid pathway connectors. These components may be arranged within a housing. The arrangement of these components may provide an easy to use device that is capable of delivering volumes larger than traditionally injected using syringes. Translation of a drug container of the device may cause connection of a fluid pathway from the drug container for delivery of a medicament to a target location.

20 Claims, 5 Drawing Sheets

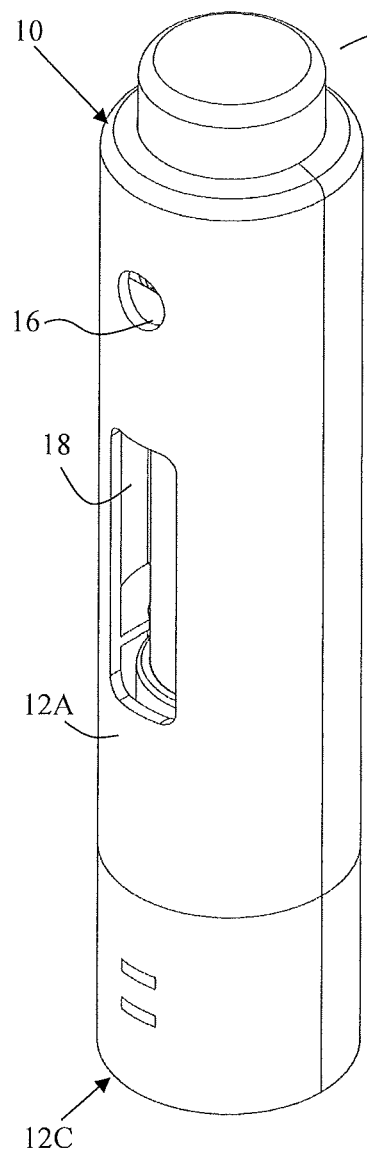
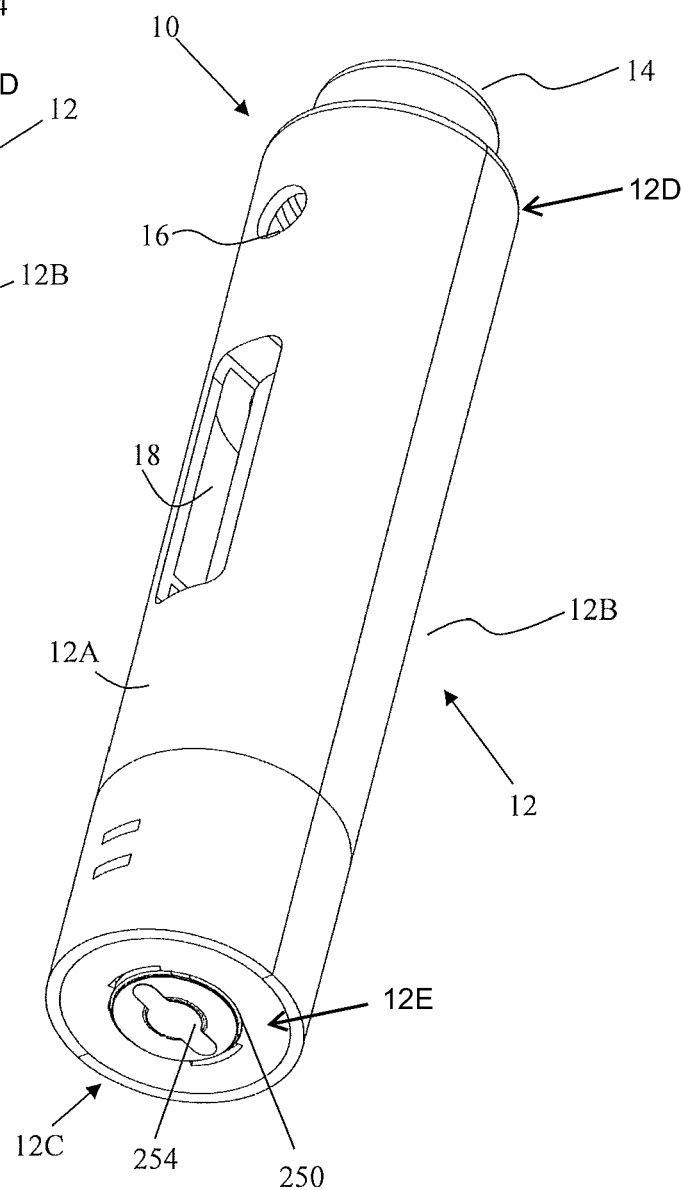
FIG. 1A
FIG. 1B

HANDHELD DRUG DELIVERY DEVICE

RELATED APPLICATION

This application is a continuation of International Application No. PCT/IB2017/001371, which designated the United States and was filed on Nov. 9, 2017, published in English.

The entire teachings of the above application are incorporated herein by reference.

FIELD

This disclosure relates to drug delivery devices. More particularly, this disclosure relates to handheld drug delivery devices; drug delivery devices with drive mechanisms, automatic needle insertion mechanisms, and fluid pathway connection mechanisms; the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. However, the volume delivered by such devices is limited. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Additionally, auto-injectors are sometimes used for parenteral delivery of drugs. These auto-injectors allow the automated delivery of a medicament while shielding the delivery needle from the patient's view. These devices typically utilize syringe type drug containers. As a result, the total volume of drug is limited. Additionally, the maximum delivery force is limited in order to avoid breakage of the container. As a result, there is a need for a large volume drug delivery device which is convenient for the user and cost effective to manufacture.

SUMMARY

The present disclosure provides handheld drug delivery devices for injection of a medicament into a target location. The drug delivery devices of the present disclosure include drive mechanisms, needle insertion mechanisms, and fluid pathway connectors. These components may be arranged within a housing. The arrangement of these components may provide an easy to use device that is capable of delivering volumes larger than traditionally injected using syringes. Additionally, the delivery time may be controlled by the device configuration, limiting variability. This delivery time may, if desired, be less than with traditional syringes and syringe based auto-injectors. Additionally, the drug delivery devices of the present disclosure may be convenient and easy to use even for patients with reduced dexterity or motor control.

In some embodiments, the drug delivery device includes an activation mechanism; a drive mechanism including a biasing member; a drug container defining a longitudinal axis; a fluid pathway connector including a piercing member; a needle insertion mechanism including an insertion needle; and a housing, the drive mechanism, the fluid pathway connector, and the needle insertion mechanism disposed within the housing. In at least some embodiments, the longitudinal axis of the drug container, the piercing member, and the insertion needle are substantially parallel.

In some embodiments, the drug delivery device further includes a plunger seal disposed in the drug container. The biasing member of the drive mechanism is configured to apply a force on the plunger seal in response to actuation of the activation mechanism, the force directed toward a distal end of the drug container. Additionally, the drug container is configured to translate in the distal direction in response to the force applied to the plunger seal. The drug delivery device can also include a pierceable seal disposed at the distal end of the drug container and displacement of the drug container causes the piercing member of the fluid pathway connector to pierce the pierceable seal to open a fluid pathway from the drug container, through the piercing member and to the needle insertion mechanism.

In some embodiments, the needle insertion mechanism includes an insertion biasing member which causes the insertion needle to extend in the distal direction in response to the translation of the drug container.

Further, the drug delivery device may be configured such that the needle insertion mechanism is able to translate and/or rotate with respect to one or more of the drive mechanism, drug container, and fluid pathway connection. As a result, movements introduced to the drug delivery device, by the user, may not result in movement of the needle and/or cannula disposed in the target site. This may reduce pain to the patient during injection.

The drug delivery devices may include an activation mechanism that initiates one or more of activation of a drive mechanism, insertion of a needle and/or cannula into a target site, and connection of a fluid pathway from a drug container to the needle insertion mechanism. The activation mechanism may directly or indirectly cause one or more of these steps. In at least one embodiment, activation of the drive mechanism causes translation of the drug container. This translation of the drug container causes a piercing member of the fluid pathway connector to pierce a pierceable seal of the drug container, thereby opening a fluid path from the drug container to the needle insertion mechanism. Additionally, translation of the drug container may cause activation of the needle insertion mechanism to insert the needle and/or cannula into the target site.

At least some embodiments of the present drug delivery devices provide the necessary drive force to push a plunger seal and a drug fluid within a drug container, while reducing or minimizing the drive mechanism and overall device footprint. Accordingly, the present drug delivery devices may provide a drive mechanism which may be utilized within a more compact drug delivery device. Some embodiments of the present drug delivery device may similarly be utilized to provide additional force, as may be needed for highly viscous drug fluids or for larger volume drug containers.

BRIEF DESCRIPTION OF THE DRAWINGS

These and other features and advantages of the present drug delivery devices will be more fully disclosed in, or rendered obvious by, the following detailed description of the preferred embodiments of the drug delivery device, which is to be considered together with the accompanying drawings wherein like numbers refer to like parts and further wherein:

FIG. 1A shows an isometric view of a drug delivery device according to one embodiment of the present disclosure;

FIG. 1B shows an additional view of the drug delivery device shown in FIG. 1A;

DETAILED DESCRIPTION

Figure 2A:
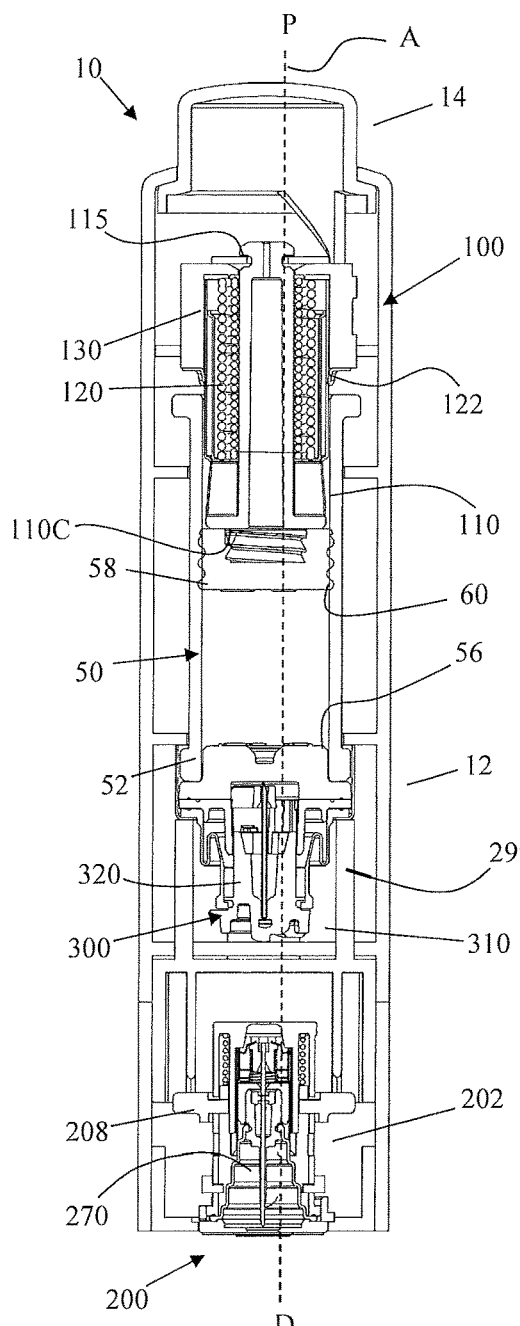
FIG. 2A is a side cross-sectional view of the drug delivery device shown in FIG. 1A in an initial configuration.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present drug delivery device may include one or more additional components which may be considered standard components in the industry of medical devices. The components, and the embodiments containing such components, are within the contemplation of the present disclosure and are to be understood as falling within the breadth and scope of the present disclosure.

As used herein to describe the drive mechanisms, drug delivery devices, or any of the relative positions of the components of the present delivery devices, the terms "axial" or "axially" refer generally to a longitudinal axis "A" around which the drive mechanisms are preferably positioned, although not necessarily symmetrically therearound. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of syringes. According to various aspects and embodiments described herein, reference is made to a "biasing member", such as in the context of one or more biasing members for insertion or retraction of the needle, trocar, and/or cannula. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present device, the biasing member is a spring, preferably a compression spring. For the purposes of this disclosure and its claims, when used in connection with biasing members, be it a specific embodiment of biasing members, such as springs, or the general use of the term "biasing members," the terms "parallel" are to be interpreted as they would by those of skill in the art. That is, the terms "series," "in series," or "disposed in series" is to be interpreted as springs disposed and operating as they would when connected end to end, and the terms "parallel," "in parallel," or "disposed in parallel" is to be interpreted as springs disposed and operating as they would in a side-by-side relationship.

The novel devices of the present disclosure are safe and easy to use, and are aesthetically and ergonomically appealing for self-administering patients. The devices described herein incorporate features which make activation, operation, and lock-out of the device simple for even untrained users. The novel devices of the present disclosure provide these desirable features without any of the problems associated with known prior art devices. Additionally, a handheld drug delivery device as described herein provides a number of advantages over traditional syringes or syringe based auto-injectors. For example, a large volume of medicament may be delivered to the patient in a pre-defined period of time. This time may, if desired, be shorter than possible with a traditional syringe. This shorter delivery time may result in a more convenient experience for patients. Certain non-limiting embodiments of the novel drug delivery devices, drive mechanisms, and their respective components are described further herein with reference to the accompanying figures.

FIGS. 1A-1B show an exemplary drug delivery device according to at least one embodiment of the present disclosure. The drug delivery device 10 may be utilized to administer delivery of a drug treatment into a body of a user. As shown in FIGS. 1A-1B, the drug delivery device 10 includes a housing 12. The housing 12 may include one or more housing subcomponents which are fixedly engageable to facilitate easier manufacturing, assembly, and operation of the drug delivery device 10. For example, the drug delivery device 10 includes a housing 12 which includes a left housing 12A and a right housing 12B. Additionally, or alternatively, the housing may include an upper housing and lower housing. The drug delivery device 10 may further include an activation mechanism 14, a status indicator 16, and a window 18. The window 18 may be any translucent or transmissive surface through which the operation of the drug delivery device 10 may be viewed. As shown in FIGS. 2A-2C and 7, the drug delivery device 10 further includes a sterile fluid conduit 30, a drive mechanism 100, a drug container 50, an insertion mechanism 200, a fluid pathway connection 300, and a power and a control system (not shown). One or more of the components of such drug delivery devices may be modular in that they may be, for example, pre-assembled as separate components and configured into position into the housing 12 of the drug delivery device 10 during manufacturing.

By aligning the drive mechanism 100, fluid pathway connection 300, and needle insertion mechanism 200 such that they are substantially coaxial, the overall dimensions of the drug delivery device 10 may be minimized. Additionally, this configuration may provide a compact, convenient, and ergonomic form factor, which is easily handled by patients. Such a device may be easily used by patients with reduced or compromised dexterity or motor control.

The housing 12 encases the device components. The housing 12 also provides protection to the interior components of the device 10 against environmental influences. The housing 12 is ergonomically and aesthetically designed in size, shape, and related features to facilitate easy packaging, storage, handling, and use by users who may be untrained and/or physically impaired. Furthermore, the external surface of the housing 12 may be utilized to provide product labeling, safety instructions, and the like. Additionally, as described above, the housing 12 may include certain components, such as the status indicator 16 and the window 18, which may provide operation feedback to the user.

In at least one embodiment, the drug delivery device 10 provides an activation mechanism 14 that is displaced by the user to trigger the start of drug delivery. In a preferred embodiment, the activation mechanism is a start button 14 that is located through the housing 12, such as through an aperture between the left housing 12A and the right housing 12B, extending from the proximal end of the housing, and which contacts a retainer 115 of the drive mechanism 100. In at least one embodiment, the start button 14 may be a push button, and in other embodiments, may be an on/off switch, a toggle, or any similar activation feature known in the art. In some embodiments, one or more of the activation mechanism 14, the status indicator 16, the window 18, and combinations thereof may be provided on the left housing 12A or the right housing 12B such as, for example, on a side visible to the user when the drug delivery device 10 is placed against the body of the user. The housing 12 is described in further detail hereinafter with reference to other components and embodiments of the present disclosure.

The drug delivery device 10 is configured such that, upon activation by a user by depression of the activation mechanism 14, the drug delivery device 10 is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. In one embodiment, a single depression of the activation mechanism 14 initiates the insertion of a fluid pathway into the user, fluidly connects the drug container to the fluid conduit, and initiates the delivery of the drug fluid. In other embodiments, one or more of these steps may be initiated by a separate depression of the activation mechanism 14. Alternatively, the drug delivery device 10 may include two or more activation mechanisms. For example, the drug delivery device 10 may include a needle insertion mechanism (NIM) activation mechanism, which is operable by the user to initiate insertion of the fluid pathway into the body of the user. Such a NIM activation mechanism may be located adjacent to the activation mechanism 14 or, alternatively, may be positioned on the side of the drug delivery device 10. In an embodiment with multiple activation mechanisms, the drug delivery device 10 may be configured such that they must be operated in a predefined sequence.

Further, optionally, the housing 12 may include an articulating portion (not shown). The articulating portion may be positioned such that movement of a distal end 12C of housing 12 may move relative to a proximal portion 12D of the housing 12. This may allow relative movement between the needle insertion mechanism 200 and the fluid pathway connection 300. The fluid conduit 30 may be configured to allow such movement. The articulating portion may be constructed of an elastomeric material or any other relatively less rigid material that would allow flexion. Alternatively, the flexible portion may be constructed of a substantially similar material as the remainder of the housing but may be relatively flexible due to the mechanical design of the housing. For example, the flexible portion may consist of a thinner outside wall. In such an embodiment, a cover may be provided over the flexible portion to reduce potential pinching hazards. In some embodiments, the cover can be constructed of an elastomeric material.

In such an embodiment, the position of the needle and/or cannula within the target will not be affected by movement of the proximal portion 12D of the housing 12, for example movement introduced by the user. As a result, user discomfort may be reduced. This may provide a significant benefit to all users but specifically those with compromised dexterity and/or motor control who have difficulty holding an injector or syringe in place during injection. A distal face 12E of housing 12 or needle insertion mechanism 200 can include an adhesive surface to maintain the position of the needle insertion mechanism 200 with respect to the target.

In another embodiment, relative movement between the needle insertion mechanism 200 and the drug container is enabled by a mechanical coupling, such as a universal joint or ball and socket configuration. Such a mechanical coupling may connect the proximal portion 12D and the distal portion 12C. Alternatively, the needle insertion mechanism 200 may be coupled to the fluid pathway connection or drug container by such a coupling. For example, the housing 202 of the needle insertion mechanism 200 may be mechanically coupled to the connection hub 310 of the fluid pathway connection. Alternatively, the needle insertion mechanism 200 may be mechanically coupled to the housing 12 in such a way that the needle insertion mechanism 200 may translate and/or rotate relative to the housing. For example, needle insertion mechanism 200 may be permitted to float within housing 12.

The power and control system may include a power source, which provides the energy for various electrical components within the drug delivery device, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system controls several device interactions with the user and interfaces with the drive mechanism 100. The power and control system may also interface with the status indicator 16 of the housing 12, which may be a transmissive or translucent material which permits light transfer, to provide visual feedback to the user. The power and control system interfaces with the drive mechanism 100 through one or more interconnects to relay status indication, such as activation, drug delivery, and end-of-dose, to the user. Such status indication may be presented to the user via auditory tones, such as through audible alarms, and/or via visual indicators, such as through the LEDs. In a preferred embodiment, the control interfaces between the power and control system and the other components of the drug delivery device are not engaged or connected until activation by the user. This is a desirable safety feature that prevents accidental operation of the drug delivery device 10 and may additionally maintain the energy contained in the power source during storage, transportation, and the like.

The power and control system may be configured to provide a number of different status indicators to the user. For example, the power and control system may be configured such that after the on-body sensor and/or trigger mechanism have been pressed, the power and control system provides a ready-to-start status signal via the status indicator 16 if device start-up checks provide no errors. During the drug delivery process, the power and control system is configured to provide a dispensing status signal via the status indicator 16. After the drug has been administered into the body of the user and after the end of any additional dwell time, to ensure that substantially the entire dose has been delivered to the user, the power and control system may provide an okay-to-remove status signal via the status indicator 16. This may be independently verified by the user by viewing the drive mechanism and drug dose delivery through the window 18 of the housing 12. Additionally, the power and control system may be configured to provide one or more alert signals via the status indicator 16, such as for example alerts indicative of fault or operation failure situations.

In one embodiment, the fluid pathway connection 300 includes a sterile fluid conduit 30, a piercing member 330, a connection hub 310, and a sterile sleeve 320. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drug container 50. The sterility of this connection may be maintained by performing the connection within a flexible sterile sleeve. Upon substantially simultaneous activation of the insertion mechanism 200, the fluid pathway between the drug container 50 and the insertion mechanism 200 is complete to permit drug delivery into the body of the user.

In other embodiments, the fluid pathway connection may be as described in U.S. application Ser. No. 13/612,203, U.S. application Ser. No. 13/796,156, U.S. application Ser. No. 14/466,403, or PCT Appl. No. PCT/US2016/020486, which are incorporated herein by reference in their entirety.

The drug delivery device is capable of delivering a range of drugs with different viscosities and volumes. The drug delivery device is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof.

A number of insertion mechanisms may be utilized within the drug delivery devices of the present disclosure. In at least one embodiment, the insertion mechanism 200 includes an insertion mechanism housing 202 having one or more lock-out windows 202A, and a base 250 for connection to the housing (as shown in FIG. 2A). The connection of the base 250 to the housing 12 may be, for example, such that the bottom of the base 250 is permitted to pass-through a hole in the housing 12 to permit direct contact of the base 250 to the body of the user. In such configurations, the bottom of the base 250 may include a sealing membrane that is removable prior to use of the drug delivery device 10. The insertion mechanism may further include one or more insertion biasing members 260, a needle 210, a retraction biasing member 220, a cannula 230, and a manifold 240. The manifold 240 may connect to sterile fluid conduit 30 to permit fluid flow through the manifold 240, cannula 230, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 27-gauge solid core trocar and in other embodiments, the needle may be any size needle suitable to insert the cannula for the type of drug and drug administration (e.g., subcutaneous, intramuscular, intradermal, etc.) intended. A sterile boot 270 can be utilized within the needle insertion mechanism 200. The sterile boot 270 is a collapsible sterile membrane that is in fixed engagement at a proximal end with the manifold 240 and at a distal end with the base 250. In at least one embodiment, the sterile boot 270 is maintained in fixed engagement at a distal end between base 250 and insertion mechanism housing 202. Base 250 includes a base opening through which the needle 210 and cannula 230 may pass-through during operation of the insertion mechanism 200. Sterility of the cannula 230 and needle 210 are maintained by their initial positioning within the sterile portions of the insertion mechanism 200. Specifically, as described above, the needle 210 and cannula 230 are maintained in the sterile environment of the manifold 240 and sterile boot 270. The base opening of the base 250 may be closed from non-sterile environments as well, such as by for example a sealing membrane 254 (shown in FIG. 1B).

According to at least one embodiment of the present disclosure, the insertion mechanism is initially locked into a ready-to use-stage by lockout pin(s) 208 which are initially positioned within lockout windows 202A of the insertion mechanism housing 202. In this initial configuration, insertion biasing member 260 and retraction biasing member 220 are each retained in their compressed, energized states. Depression of the activation mechanism 14 may directly or indirectly cause displacement of lockout pin(s) 208 from their initial position within lockout windows 202A of insertion mechanism housing 202 as described above. Displacement of the lockout pin(s) 208 permits insertion biasing member 260 to decompress from its initial compressed, energized state. This decompression of the insertion biasing member 260 drives the needle 210 and the cannula 230 into the body of the user. At the end of the insertion stage, the retraction biasing member 220 is permitted to expand in the proximal direction from its initial energized state. This axial expansion in the proximal direction of the retraction biasing member 220 retracts the needle 210, while maintaining the cannula 230 in fluid communication with the body of the user. Accordingly, the insertion mechanism may be used to insert a needle 210 and cannula 230 into the user and, subsequently, retract the needle 210 while retaining the cannula 230 in position for drug delivery to the body of the user.

Alternatively, the needle insertion mechanism 200 may include a hollow needle which is retained in position for drug delivery to the body of the user. In such an embodiment, retraction of the needle may occur at completion of drug delivery. This may occur automatically or, alternatively, may be initiated by an action of the user, such as a secondary depression of the activation mechanism.

In other embodiments, the insertion mechanism may be as described in U.S. Pat. No. 9,511,189, PCT Appl. No. PCT/US2015/052815, or PCT Appl. No. PCT/US2016/017534, which are incorporated herein by reference, in their entirety.

Figure 2B:
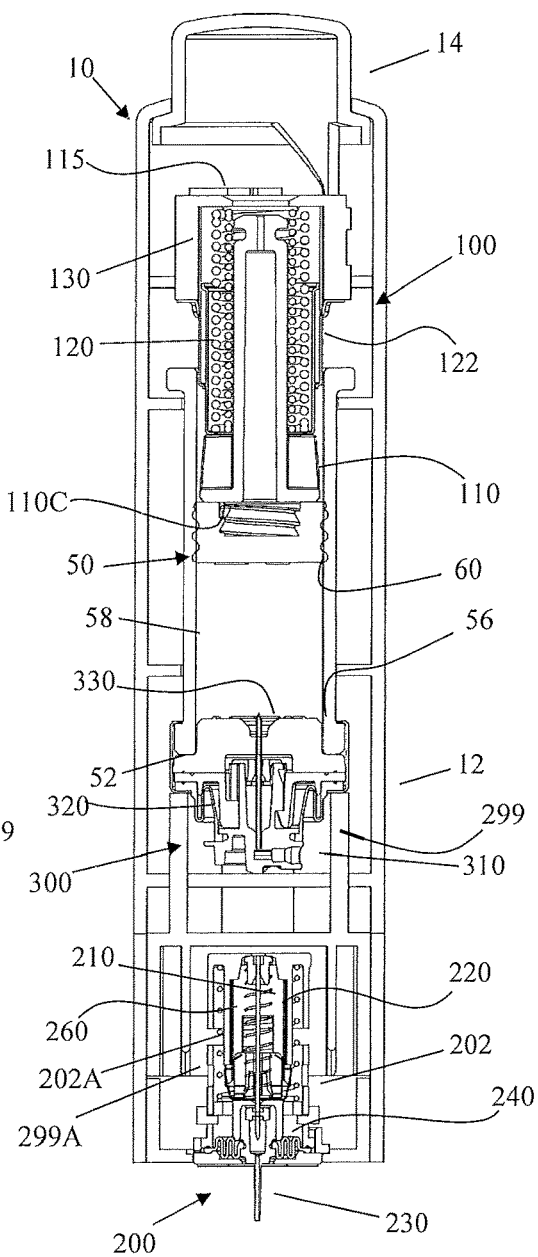
FIG. 2B is a side cross-sectional view of the drug delivery device of FIG. 1A in an activated configuration.
Figure 2C:
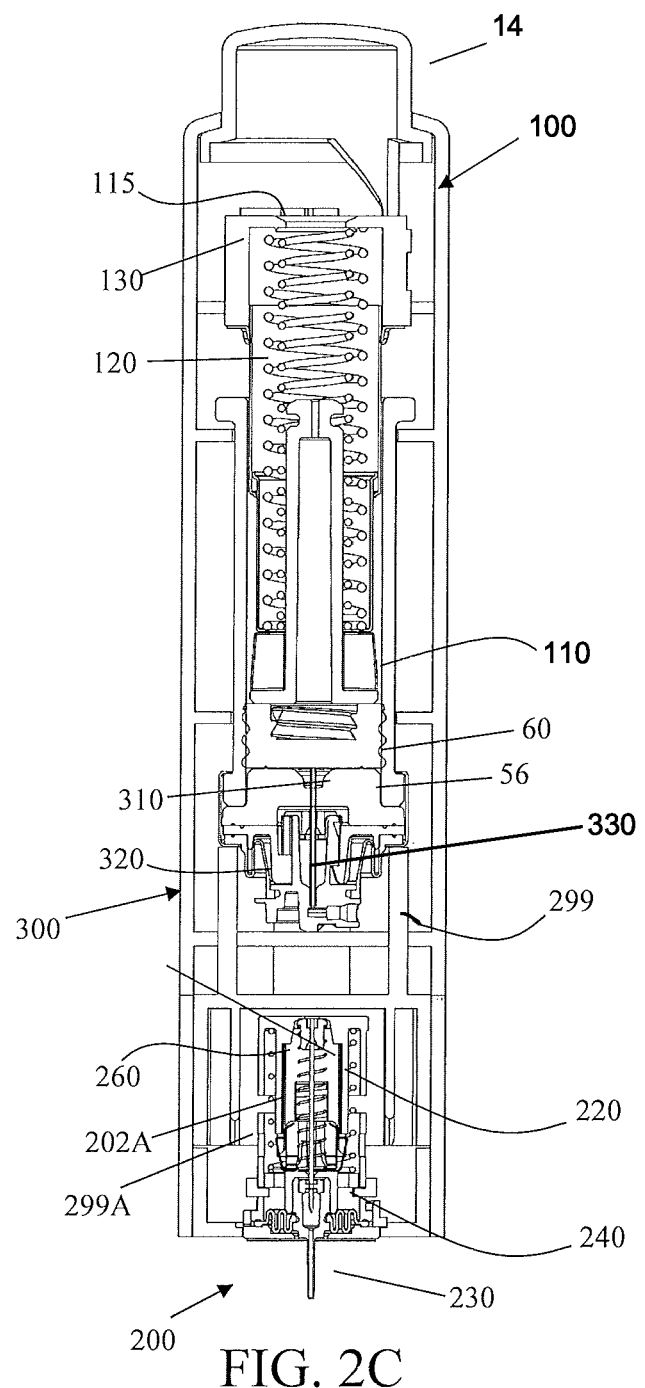
FIG. 2C is a side cross-sectional view of the drug delivery device of FIG. 1A in an end of dose configuration.
Figure 3:
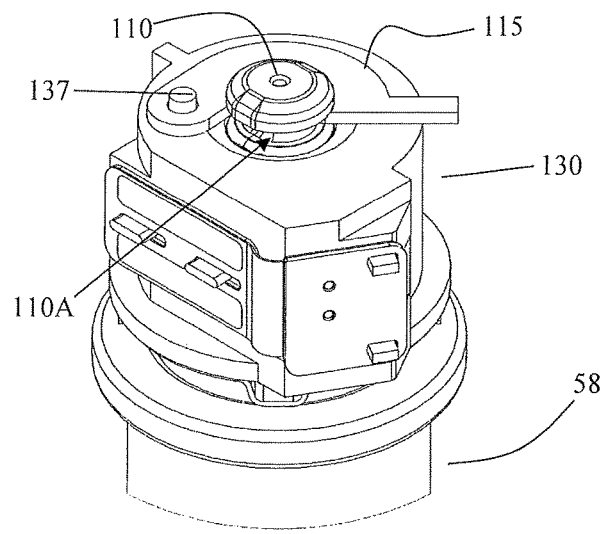
FIG. 3 is a detailed isometric view of one embodiment of a drive mechanism and retainer in an initial, locked configuration.
Figures 4, 5:
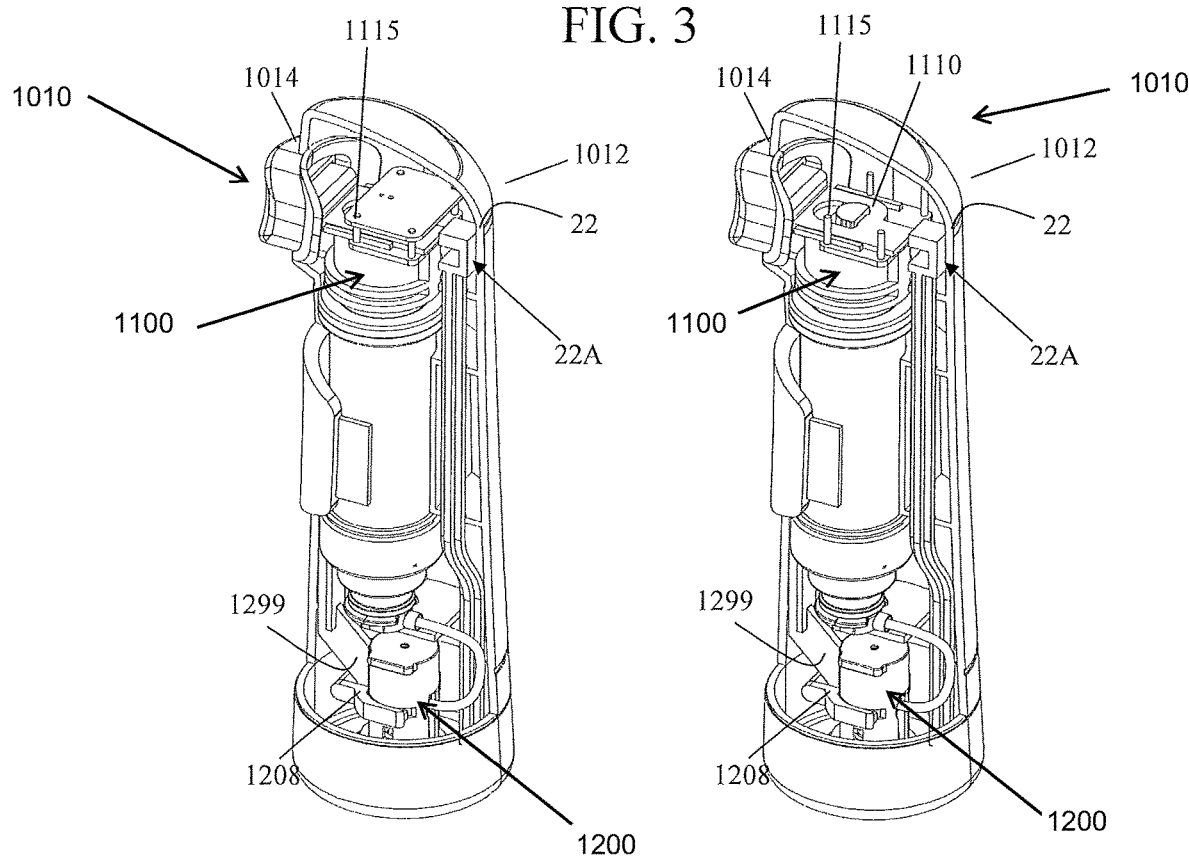
FIG. 4 is an isometric view of a drug delivery device according to another embodiment in which a portion of the housing is hidden.
FIG. 5 is an additional isometric view of the drug delivery device of FIG. 4 in which a portion of the housing and certain internal components are hidden.
Figure 6:
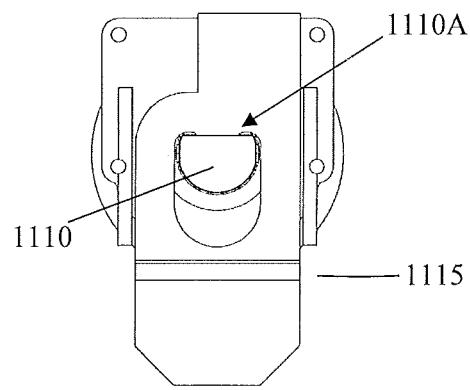
FIG. 6 is a top view of one embodiment of a retainer and drive mechanism in an initial, locked configuration.

With reference to the embodiments shown in FIGS. 2 and 3, drive mechanism 100 includes a drive housing 130. The drive mechanism 100 is engaged with a drug container 50 having a cap 52, a pierceable seal 56, a barrel 58, and a plunger seal 60. The drug container 50 may contain a drug fluid, within the barrel 58 between the pierceable seal 56 and the plunger seal 60, for delivery through the insertion mechanism 200 and drug delivery device 10 into the body of the user. The seals described herein may be comprised of a number of materials but are, in a preferred embodiment, comprised of one or more elastomers or rubbers. The drive mechanism 100 may further contain one or more drive biasing members, one or more release mechanisms, and one or more guides. The components of the drive mechanism function to force a fluid from the drug container out through the pierceable seal 56, or preferably through the piercing member 330 of the fluid pathway connection 300, for delivery through the fluid pathway connection 300, sterile fluid conduit 30, and insertion mechanism 200 into the body of the user.

The drug container 50 is mounted to a distal end of the drive housing 130. Compressed within the drive housing 130, between the drug container 50 and the proximal end of the housing 130, are a drive biasing member 122 and a piston 110, wherein the drive biasing member 122 is configured to bear upon an interface surface 110C of the piston 110. Optionally, a cover sleeve 120 may be utilized between the drive biasing member 122 and the interface surface 110C of the piston 110 to, for example, promote more even distribution of force from the drive biasing member 122 to the piston 110, prevent buckling of the drive biasing member 122, and/or hide biasing member 122 from user view. Interface surface 110C of piston 110 is caused to rest substantially adjacent to, or in contact with, a proximal end of the plunger seal 60.

The drive mechanism 100 may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power and control system. Such components may be utilized within the drive mechanism to measure and relay information related to the status of operation of the drive mechanism, which may be converted by the power and control system into tactile, auditory, and/or visual feedback to the user.

In one particular embodiment, the drive mechanism 100 employs one or more compression springs as the biasing member(s). Upon activation of the drug delivery device 10 by the user, the compression spring(s) may be directly or indirectly released from an energized state. For example, as shown in FIG. 2A, expansion of the biasing member(s) 122 may be initially restricted by the interaction of the retainer 115 with the piston 110. When positioned within a locking groove 110A of the piston 110, the retainer 115 prevents axial translation of the piston. In one embodiment, shown in FIG. 3, the retainer 115 is a rotational retainer able to rotate about a pivot member 137. The pivot member 137 may be, for example, a protrusion extending from the housing 130 or, alternatively, a pin or other component affixed or attached to the housing 130. In such an embodiment, displacement of the activation mechanism may cause the retainer 115 to rotate about the pivot member 137 and disengage the locking groove 110A of the piston 110, thereby releasing the piston to axially translate. Upon release, the compression spring(s) 122 may bear against and act upon the plunger seal 60 to force the fluid drug out of the drug container 50.

The novel drive mechanisms of the present disclosure integrate status indication into the drug dose delivery. By use of one or more status switch interconnects and one or more corresponding electrical contacts, the status of the drive mechanism before, during, and after operation can be relayed to the power and control system to provide feedback to the user. Such feedback may be tactile, visual, and/or auditory, as described above, and may be redundant such that more than one signal or types of feedback are provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug delivery device 10 may provide an end-of-dose indication. As the end-of-dose indication is tied to the piston reaching the end of its axial translation, the drive mechanism and drug delivery device 10 provide a true end-of-dose indication to the user.

In this embodiment, the biasing members 122 are in the form of a pair of concentrically disposed compression springs. Alternate arrangements are envisioned, however. For example, one or more of the biasing members could alternately, for example, be tension springs, depending upon the structure of the components of the drive mechanism.

Moreover, in the illustrated drive mechanism 100, the biasing members 122 are disposed concentrically with respect to each other and the piston 100. In an alternate embodiment, however, the biasing members may be alternately disposed, as, by way of example only, in a side by side arrangement, or on opposite sides of the piston. In still further embodiments, three or more biasing members could be provided and disposed in parallel in any appropriate configuration. It will further be appreciated, that an additional biasing member may be provided and disposed in series with one or more of the parallelly disposed biasing members.

It will be appreciated by those of skill in the art that the embodiments of the present disclosure provide the necessary drive force to push a plunger seal and a drug fluid within a drug container, while reducing or minimizing the drive mechanism and overall device footprint. Accordingly, the present disclosure provides a drive mechanism which may be utilized within a more compact drug delivery device. The embodiments of the present disclosure may similarly be utilized to provide additional force, as may be needed for highly viscous drug fluids or for larger volume drug containers.

The drive mechanism may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power control system.

In one embodiment, depression of the activation mechanism 14 causes the drive housing 130 and/or drug container 50 to translate axially in the distal direction. This distal translation may be caused directly by the depression of the activation mechanism 14 such as by contact of a portion of the activation mechanism 14 with the drug container 50 or drive housing 130. Alternatively, or additionally, as shown in FIGS. 2A-2C, the translation of the drug container 50 is caused by de-energizing of the drive biasing member 122. In such an embodiment, depression of the activation mechanism 14 causes the retainer 115 to disengage the piston 110, thereby allowing decompression of the drive biasing member 122. Initially, the fluid pathway connection 300 has not been activated and the contents of the drug container 50 are unable to flow out of the drug container 50. Because the fluid pathway connection 300 has not been opened, and the volume of the contents of the drug container 50 are therefore fixed, translation of the piston 110 with respect to the drug container 50 is restricted. Hence, translation of the piston 110, caused by de-energizing of the drive biasing member 122, is transmitted, by hydraulic and/or pneumatic pressure within the drug container 50, into translation of the drug container 50 in the distal direction. This hydraulic and/or pneumatic pressure causes the drug container 50 to translate in the distal direction until the piercing member 330 of the fluid pathway connection 300 pierces the pierceable seal 56, thereby opening a fluid flowpath from the drug container 50. The fluid pathway connection hub 310 is restricted from translating in the distal direction by contact with one or more aspects of housing 12.

Additionally, translation of the drug container 50 may cause activation of the needle insertion mechanism 200. In the embodiment shown in FIGS. 2A-2C, a portion of the drug container 50 or the fluid pathway connection 300 contacts an activator 299. Translation of the drug container 50 causes translation of the activator 299, which results in activation of the needle insertion mechanism 200. In one such embodiment, the activator 299 includes guide arms 299A which have a ramped surface which engages protrusions 208A of the lockout pin 208. Translation of the activator 299 causes displacement of the lockout pin 208 with respect to the lockout windows 202A of housing 202, thereby allowing insertion of the needle and/or cannula 230 into the target as shown in FIG. 2B. Alternatively, the lockout pin 208 may be biased, such as by a spring, to displace out of engagement with the lockout windows 202A, such movement initially being restricted by contact with the activator 299. Translation of the activator 299 thereby allows displacement of the lockout pin 208 and firing of the needle insertion mechanism 200.

In another embodiment, activator 299 is translationally coupled with the activation mechanism 14. In such an embodiment, depression of the activation mechanism 14 causes distal translation of the activator 299, which in turn causes activation of the needle insertion mechanism 200, as described above.

An alternative embodiment is shown in FIGS. 4-7. In these figures, in some instances, reference numerals 1xxx are used to signify components or features similar to those described in the preceding embodiment. In this embodiment, an activation mechanism 1014 is positioned on the front face of drug delivery device 1010. The activation mechanism 1014 is engaged with the retainer 1115, which initially prevents translation of the piston 1110. As shown best in FIGS. 6 and 7, the retainer 1115 is initially engaged with a locking groove 1110A of the piston 1110. This engagement prevents translation of the piston 1110. Depression of the activation mechanism causes displacement of the retainer 1115, such that the retainer 1115 disengages the locking groove 1110A and, thereby, releases the piston 1110 to translate in response to decompression of the drive biasing member 1122.

Figure 7:
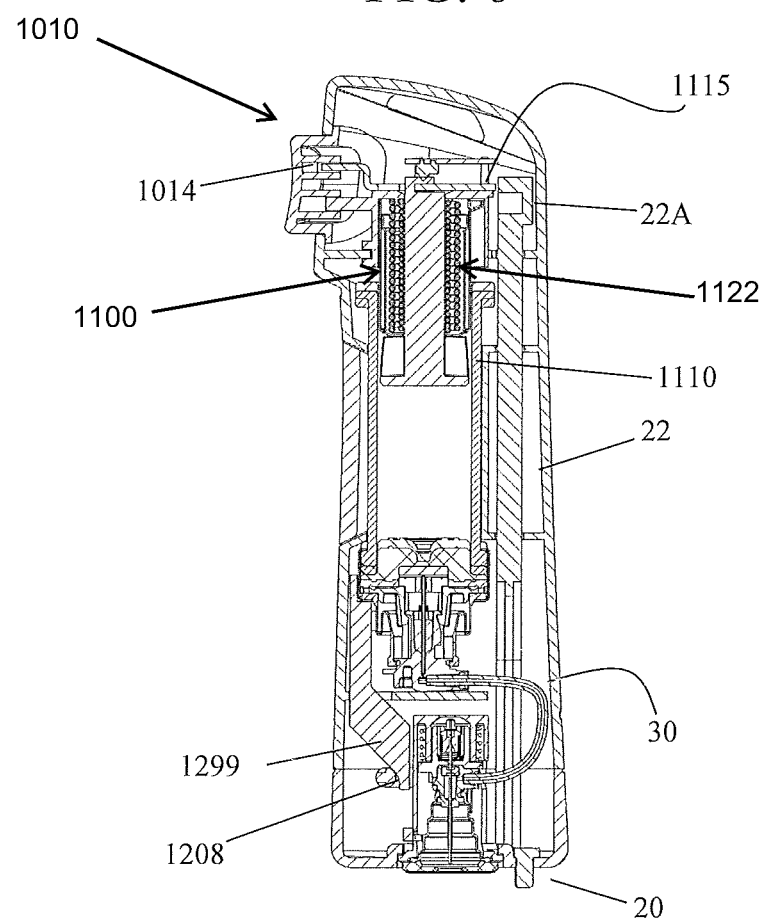
FIG. 7 is a side cross-sectional view of the drug delivery device of FIG. 4 in an initial, locked configuration.

One or more optional safety mechanisms may be utilized, for example, to prevent premature activation of the drug delivery device. Accordingly, in at least one embodiment, the on-body sensor is a mechanical safety mechanism, such as for example a mechanical interlock, that prevents triggering of the drug delivery device 10 by the activation mechanism 14. For example, as shown in FIGS. 4-7, an optional on-body sensor 20 can be provided as a safety feature to ensure that the drive mechanism 1100, needle insertion mechanism 1200, or the activation mechanism 1014, cannot be engaged unless the drug delivery device 1010 is in contact with the body of the user. In one such embodiment, the on-body sensor 20 is located on the distal face of the housing 1012 where it may come in contact with the user's body. Prior to depression of the on-body sensor, depression of the activation mechanism is mechanically restricted. As shown in FIG. 7, displacement of the retainer 1115 is initially prevented by contact with an extension arm 22 of the on-body sensor 20. As a result, with the on-body sensor 20 in this position, activation of the delivery device 1010 is prevented. Upon activation of the on-body sensor, depression of the activation mechanism is permitted. When the distal face 12E of the delivery device 1010 is brought into contact with the target site, the on-body sensor 20 is depressed and the extension arm 22 moves in the proximal direction. As a result, the retainer 1115 is aligned with an aperture 22A of the extension arm 22 to allow displacement of the retainer 1115 and activation of delivery. In some versions, activation causes translation of an activator 1299, which results in release of a lock-out pin 1208 (seen in FIGS.

4, 5, and 7) and activation of the needle insertion mechanism 1200 in a manner similar to that described above with respect to FIGS. 2A-2C.

In another embodiment, the on-body sensor may be an electro-mechanical sensor such as a mechanical lock out that sends a signal to the power and control system to permit activation. In still other embodiments, the on-body sensor can be electrically based such as, for example, a capacitive- or impedance-based sensor which must detect tissue before permitting activation of the power and control system. These concepts are not mutually exclusive and one or more combinations may be utilized within the breadth of the present disclosure to prevent, for example, premature activation of the drug delivery device.

One or more of the components of drug delivery device may be modified while remaining functionally within the breadth and scope of the present disclosure. For example, as described above, while the housing of drug delivery device is shown as two separate components left housing and right housing, these components may be a single unified component. As discussed above, a glue, adhesive, or other known materials or methods may be utilized to affix one or more components of the drive mechanism and/or drug delivery device to each other. Alternatively, one or more components of the drive mechanism and/or drug delivery device may be a unified component. For example, the left housing and right housing may be separate components affixed together by a glue or adhesive, a screw fit connection, an interference fit, fusion joining, welding, ultrasonic welding, and the like; or the left housing and right housing may be a single unified component. Such standard components and functional variations would be appreciated by one having ordinary skill in the art and are, accordingly, within the breadth and scope of the present disclosure.

It will be appreciated from the above description that the drug delivery devices disclosed herein provide an efficient and easily-operated system for automated drug delivery from a drug container. Furthermore, the novel configurations of the drug delivery devices of the present disclosure maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present device, the power and control system, the activation mechanism, the housing, and other components of the drug delivery device do not need to be sterilized. This greatly improves the manufacturability of the device and reduces associated assembly costs. Accordingly, the devices of the present disclosure do not require terminal sterilization upon completion of assembly.

Manufacturing of a drug delivery device includes the step of attaching both the drive mechanism and drug container, either separately or as a combined component, to the housing of the drug delivery device. The method of manufacturing further includes attachment of the fluid pathway connection, drug container, and insertion mechanism to the assembly platform or housing. The additional components of the drug delivery device, as described above, including the power and control system, the activation mechanism, and the control arm may be attached, preformed, or pre-assembled to the housing.

Assembly and/or manufacturing of the drive mechanism, the drug delivery device, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

A method of operating the drug delivery device includes the steps of: activating, by a user, the activation mechanism; actuating an insertion mechanism; and actuating a drive mechanism to drive fluid drug flow through the drug delivery device. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the drive control mechanism and drug container to force fluid drug flow through the drug container, the fluid pathway connection, a sterile fluid conduit, and the insertion mechanism for delivery of the fluid drug to the body of a user. The method of operation of the insertion mechanism and the drug delivery device may be better appreciated with reference to FIGS. 2A-2C, as described above.

The embodiments shown and detailed herein disclose only a few possible variations of the present device; other similar variations are contemplated and incorporated within the breadth of this disclosure. Throughout the specification, the aim has been to describe the preferred embodiments of the delivery device without limiting the invention to any one embodiment or specific collection of features. Various changes and modifications may be made to the embodiments described and illustrated without departing from the present disclosure. The disclosure of each patent and scientific document, computer program and algorithm referred to in this specification is incorporated by reference in its entirety.

The invention claimed is:
1. A drug delivery device comprising:
  a housing having a proximal end and a distal end;
  an activation mechanism disposed at the proximal end of the housing;
  a drive mechanism disposed in the housing the drive mechanism including a biasing member;
  a drug container disposed in the housing, the drug container defining a longitudinal drug container axis;
  a fluid pathway connection disposed in the housing, the fluid pathway connection including a piercing member defining a longitudinal piercing member axis;
  a needle insertion mechanism disposed in the distal end of the housing, the needle insertion mechanism including an insertion needle defining a longitudinal insertion needle axis and further including an insertion biasing member retained in a compressed state at the distal end of the housing,
  wherein the longitudinal drug container axis, the longitudinal piercing member axis, and the longitudinal insertion needle axis are substantially coaxial; and
  a plunger seal disposed in the drug container, wherein the biasing member of the drive mechanism is configured to apply a force on the plunger seal in response to actuation of the activation mechanism, the force directed toward a distal end of the drug container, and wherein upon actuating the activation mechanism, the insertion biasing member decompresses, thereby driving and causing the insertion needle to extend in a distal direction toward the distal end of the housing.

2. The drug delivery device of claim 1, wherein the force applied by the biasing member of the drive mechanism is configured to cause the drug container to translate in the distal direction.

3. The drug delivery device of claim 2, further comprising a pierceable seal disposed at the distal end of the drug container and wherein displacement of the drug container is configured to cause the piercing member of the fluid pathway connection to pierce the pierceable seal to open a fluid pathway from the drug container, through the piercing member and to the needle insertion mechanism.

4. The drug delivery device of claim 2, wherein the insertion biasing member is configured to cause the insertion needle to extend in the distal direction in response to the translation of the drug container.

5. The drug delivery device of claim 4, further including an activator, and wherein displacement of the drug container is configured to cause the activator to displace a lockout pin of the needle insertion mechanism.

6. The drug delivery device of claim 5, wherein the activator includes a ramped surface, wherein the ramped surface is configured to cause displacement of the lockout pin in a direction perpendicular to the longitudinal axis of the drug container.

7. The drug delivery device of claim 1, wherein the housing includes an upper portion and a lower portion, the upper portion joined to the lower portion at a junction.

8. The drug delivery device of claim 7, wherein the lower portion is capable of articulation with respect to the upper portion and further wherein the needle insertion mechanism is disposed substantially within the lower portion.

9. The drug delivery device of claim 1, wherein the drive mechanism includes a retainer and a piston, the retainer being in an initial position in which it restricts translation of the piston and wherein actuation of the activation mechanism causes the retainer to release the piston.

10. The drug delivery device of claim 9, wherein the drive mechanism further includes a drive mechanism housing, the retainer configured for rotation with respect to the drive mechanism housing and wherein actuation of the activation mechanism is configured to cause rotation of the retainer to release the piston.

11. The drug delivery device of claim 1, further comprising an interlock, wherein in an initial configuration the interlock prevents actuation of the activation mechanism and wherein in a second configuration the interlock does not prevent actuation of the activation mechanism.

12. A drug delivery device comprising:
an activation mechanism;
a drive mechanism including a biasing member;
a drug container defining a longitudinal axis;
a pierceable seal disposed at a distal end of the drug container;
a plunger seal disposed in the drug container;
a fluid pathway connection including a piercing member;
a needle insertion mechanism including an insertion needle and an insertion biasing member;
a housing having a proximal end adjacent the activation mechanism and a distal end adjacent the needle insertion mechanism, wherein the drive mechanism, the fluid pathway connection, and the needle insertion mechanism are disposed within the housing; and
wherein the biasing member is configured to apply a force on the plunger seal in response to actuation of the activation mechanism, the force directed toward the distal end of the drug container, further wherein the force causes the drug container to translate in a distal direction and wherein the piercing member of the fluid pathway connection is configured to pierce the pierceable seal as a result of the translation of the drug container to open a fluid pathway from the drug container, through the piercing member and to the needle insertion mechanism,
wherein the needle insertion mechanism is disposed in the distal end of the housing, the insertion biasing member being retained in a compressed state at the distal end of the housing, wherein upon actuating the activation mechanism the insertion biasing member decompresses, thereby driving and causing the insertion needle to extend in the distal direction toward the distal end of the housing.

13. The drug delivery device of claim 12, wherein the insertion biasing member is configured to cause the insertion needle to extend in the distal direction in response to the translation of the drug container.

14. The drug delivery device of claim 13, further including an activator, and wherein displacement of the drug container is configured to cause the activator to displace a lockout pin of the needle insertion mechanism.

15. The drug delivery device of claim 14, wherein the activator includes a ramped surface, wherein the ramped surface is configured to cause displacement of the lockout pin in a direction perpendicular to the longitudinal axis of the drug container.

16. The drug delivery device of claim 12, wherein the housing includes an upper portion and a lower portion, the upper portion joined to the lower portion at a junction.

17. The drug delivery device of claim 16, wherein the lower portion is capable of articulation with respect to the upper portion and further wherein the needle insertion mechanism is disposed substantially within the lower portion.

18. The drug delivery device of claim 12, wherein the drive mechanism includes a retainer and a piston, the retainer being in an initial position in which it restricts translation of the piston and wherein actuation of the activation mechanism is configured to cause the retainer to release the piston.

19. The drug delivery device of claim 18, wherein the drive mechanism further includes a drive mechanism housing, the retainer configured for rotation with respect to the drive mechanism housing and wherein actuation of the activation mechanism is configured to cause rotation of the retainer to release the piston.

20. The drug delivery device of claim 12, further comprising an interlock, wherein in an initial configuration the interlock prevents actuation of the activation mechanism and wherein in a second configuration the interlock does not prevent actuation of the activation mechanism.

* * * * *